United States Patent [19]

Poittevin et al.

[11] 4,032,643
[45] June 28, 1977

[54] NOVEL THIAZOLE DERIVATIVES

[75] Inventors: André Poittevin, Vaires-sur-Marne; Vesperto Torelli, Maisons-Alfort, both of France

[73] Assignee: Roussel-UCLAF, Paris, France

[22] Filed: Feb. 2, 1976

[21] Appl. No.: 654,630

[30] Foreign Application Priority Data

Feb. 14, 1975 France .............................. 75.04627
Dec. 12, 1975 France .............................. 75.38063

[52] U.S. Cl. ............................ 424/270; 260/302 R
[51] Int. Cl.² ...................................... C07D 277/22
[58] Field of Search ................. 260/302 R; 424/270

[56] References Cited
UNITED STATES PATENTS 3,957,809  5/1976  Hardy et al. ....................... 424/270

*Primary Examiner*—Richard J. Gallagher
*Attorney, Agent, or Firm*—Hammond & Littell

[57] ABSTRACT

Novel substituted thiazoles of the formula

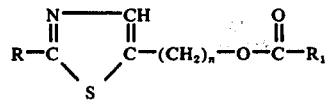

wherein R is alkyl of 1 to 5 carbon atoms and $R_1$ is selected from the group consisting of $—NH_2$, $—NH$-Alk,

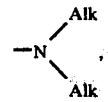

phenylamino and diphenylamino, Alk is alkyl of 1 to 4 carbon atoms and $n$ is an integer from 1 to 6 and their non-toxic, pharmaceutically acceptable acid addition salts having a marked antilipolytic activity and for some of them, a prolonged vasodilatatory activity and an antibradykinetic activity and their preparation.

15 Claims, No Drawings

NOVEL THIAZOLE DERIVATIVES

STATE OF THE ART

Zubarovskii et al [Chem. Ab., Vol. 58 (1963), p. 2525b] describes the preparation of 2-methyl-thiazole-5-methanol by reaction of ethyl 2-methyl-thiazole-5-carboxylate with lithium aluminum hydride but does not describe any pharmacological properties therefor.

Our copending commonly assigned U.S. Pat. application Ser. No. 495,556 filed Aug. 8, 1974, now U.S. Pat. No. 3,957,809, describes novel thiazole derivatives of the formula

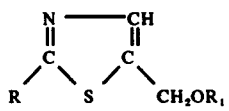

where R is alkyl of 2 to 12 carbon atoms and $R_1$ is selected from the group consisting of hydrogen, alkyl of 1 to 8 carbon atoms and acyl of an organic carboxylic acid of 1 to 12 carbon atoms having hypolipemiant activity with a very prolonged vasodilatatory activity and their preparation.

OBJECTS OF THE INVENTION

It is an object of the invention to provide the novel thiazole derivatives of formula I and the non-toxic, pharmaceutically acceptable acid addition salts and a process for their preparation.

It is another object of the invention to provide novel hypolipemiant and vasodilatatory compositions.

It is a further object of the invention to provide a novel method of inducing hypolipemic acitivity in warm-blooded animals.

These and other objects and advantages of the invention will become obvious from the following detailed description.

THE INVENTION

The novel thiazole derivatives of the invention have the formula

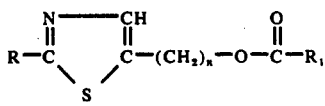

wherein R is alkyl of 1 to 5 carbon atoms and $R_1$ is selected from the group consisting of $-NH_2$, $-NH-AlK$,

phenylamino and diphenylamino, AlK is alkyl of 1 to 4 carbon atoms and n is an integer from 1 to 6 and their non-toxic, pharmaceutically acceptable acid addition salts.

Examples of R are methyl, ethyl, n-propyl, isopropyl, n-butyl, isobutyl, tert.-butyl and pentyl. Examples of suitable $-(CH_2)_n-$ groups are methylene, ethylene, propylene, butylene and pentylene. Preferably, R is alkyl of 1 to 5 carbon atoms and $R_1$ is methylamino, dimethylamino, phenylamino or diphenylamino and n is 1. Among the preferred products are 2-methyl -5-(N,N-dimethylcarbamoyloxymethyl)-thiazole, 2-methyl-5- (N-phenylcarbamoyloxymethyl)-thiazole, 2-methyl-5-(N-methylcarbamoyloxymethyl)-thiazole, 2-methyl-5-(N-methylcarbamoyloxypropyl) -thiazole and 2-propyl-5-(N-methylcarbamoyloxypentyl)-thiazole and their non-toxic, pharmaceutically acceptable acid addition salts.

Examples of suitable acids for the preparation of the acid addition salts are mineral acids such as hydrochloric acid, hydrobromic acid, hydroiodic acid, nitric acid, sulfuric acid or phosphoric acid and organic sulfonic acids such as alkylmonosulfonic acids like methanesulfonic acid, alkyldisulfonic acids such as methanedisulfonic acid, $\alpha,\beta$-ethanedisulfonic acid and arylmonosulfonic acids and aryldisulfonic acids such as benzenesulfonic acid.

The novel process of the invention for the preparation of the compounds of formula I comprises reacting a compound of the formula

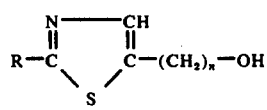

wherein R and n have the above definitions with an isocyanate of the formula $R_2-N=C=O$ wherein $R_2$ is alkyl of 1 to 4 carbon atoms or phenyl to obtain the corresponding compound of formula I wherein $R_1$ is alkylamino or phenylamino or with an acid halide of the formula

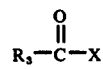

wherein X is a halogen and $R_3$ is amino, dialkylamino of 1 to 4 carbon atoms in the alkyl moiety or diphenylamino to obtain the corresponding compound of formula I wherein $R_1$ is amino, dialkylamino or diphenylamino. The compound of formula I may then be reacted with a mineral acid or sulfonic acid to obtain the corresponding acid addition salt.

The reaction of the compound of formula II with the isocyanate is preferably effected in an organic solvent such as tetrahydrofuran, toluene, benzene or cyclohexane in the optional presence of an organic base such as triethylamine, pyridine or collidine. The reaction is preferably effected at the reflux temperature.

The reaction of the compound of formula II with the acid halide is preferably effected in an organic solvent such as tetrahydrofuran, toluene, benzene or cyclohexane in the presence of a mineral or organic base such as sodium hydride, sodium amide, butyllithium, methyllithium, potassium tert.-amylate, potassium or sodium tert.-butylate, triethylamine, pyridine or collidine. The reaction is preferably effected at room temperature and the acid halide is preferably the acid chloride.

The compounds of formula II may be prepared by reducing the corresponding acids or a derivative thereof like an alkyl ester with a reducing agent such as lithium aluminum hydride or lithium borohydride in an organic solvent like tetrahydrofuran and the acids and derivatives may be prepared by the process of French Patent No. 2,047,876.

This process comprises reacting in an organic solvent an alkylthioamide of the formula

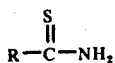

wherein R has the above definition with a compound of the formula

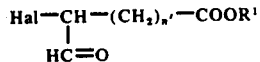

wherein Hal is chlorine or bromine, $R^1$ is alkyl of 1 to 5 carbon atoms and $n'$ is an integer from 0 to 5 to form the ester of the formula

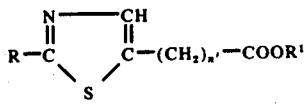

which may be hydrolyzed to obtain the corresponding free acid.

The alkylthioamides may be prepared by the process of Gilbert et al. [Chem. Ab., Vol. 65, p. 20020e] and the esters of formula A may be prepared by reacting a compound of the formula

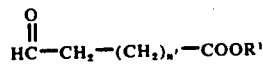

wherein $n'$ and $R_1$ have the above definition with bromine in an organic solvent or with gaseous chlorine in an organic solvent. The esters of formula C are known or may be made by hydrolyzing known esters followed by esterification.

The novel hypolipemiant compositions of the invention are comprised of an effective amount of at least one compound of formula I or a non-toxic, pharmaceutically acceptable acid addition salt thereof and a pharmaceutical carrier. The compositions may be in the form of tablets, dragees, gelules, granules, suppositories and injectable solutions or suspensions prepared in the usual manner.

The active principles may be incorporated in a known fashion into the usual excipients such as talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers or preservatives.

The compositions have a marked antilipolytic activity and reduce the level of free plasmatic fatty acids. Some of the compounds possess a prolonged vasodilatatory activity as well as an antibradykinetic activity. The compositions are therefore useful for the treatment of acute or chronic hyperlipemia, coronary insufficiency, cardic insufficiency of atheromatosis origin, chronic angina states and functional troubles of hypertension.

The novel method of the invention for inducing hypolipemic activity in warm-blooded animals, including humans, comprises administering to warm-blooded animals a hypolipemically effective amount of at least one compound of formula I or its non-toxic, pharmaceutically acceptable acid addition salts. The products may be administered orally, rectally or parenterally and the usual useful daily doses is 2 to 50 mg/kg depending upon the specific product and the method of administration.

In the following examples there are described several preferred embodiments to illustrate the invention. However, it should be understood that the invention is not intended to be limited to the specific embodiments.

EXAMPLE 1

2-methyl-5-[(N-methylcarbamoyloxy)-methyl]-thiazole

STEP A: 2-methyl-5-hydroxymethyl-thiazole 2.54 g of lithium aluminum hydride were added at 20°-25° C under a nitrogen atmosphere to a solution of 10.5 g of methyl 2-methyl-5-thiazolecarboxylate in 105 ml of anhydrous tetrahydrofuran and the mixture was refluxed for one hour and then cooled. Addition of ethyl acetate and then methanol destroyed excess hydride and the mixture was filtered. The filtrate was evaporated to dryness and the residue was chromatographed over silica gel to obtain 7.6 g of product which was crystallized from isopropyl ether to obtain 5.28 g of 2-methyl-5-hydroxymethyl-thiazole melting at 50° C.

STEP B:
2-methyl-5-[(N-methylcarbamoyloxy)-methyl]-thiazole

A mixture of 3.85 g of 2-methyl-5-hydroxymethyl-thiazole and 10 ml of methyl isocyanate stood for 24 hours and was then evaporated to dryness. The oily residue was chromatographed over silica gel and elution with a 3-7 benzene-ethyl acetate mixture yielded 5.03 g of product. The product was crystallized from a methylene chloride-isopropyl ether mixture to obtain 4.16 g of 2-methyl-5-[(N-methylcarbamoyloxy)- methyl]-thiazole in the form of colorless crystals melting at 80° C.

Analysis: $C_7H_{10}N_2O_2S$ Calculated: %C, 45.14; H, 5.41 N, 15.04; S, 17.21; Found: %C, 45.2; H, 5.5; N, 15.0; S, 17.2.

EXAMPLE 2

2-methyl-5-[(N,N-dimethylcarbamoyloxy)-methyl]-thiazole hydrochloride

A mixture of 50 ml of deperoxidized and anhydrous tetrahydrofuran and 1.9 g of sodium hydride suspended in oil was stirred and then 5.2 g of 2-methyl-5-hydroxymethyl-thiazole were added thereto followed by 8.8 g of dimethylcarbamic acid chloride while holding the temperature between 15° and 20° C. The mixture was stirred for 4 hours at room temperature and was vacuum filtered. The filter was washed with tetrahydrofuran and the filtrate was evaporated to dryness under reduced pressure. The residue was taken up in water and the aqueous phase was washed with ethyl ether. The ether extracts were dried over magnesium sulfate and evaported to dryness to obtain 10 g of raw product which was dissolved in ethyl acetate. The pH of the solution was adjusted to 1 with ethyl acetate saturated with hydrochloric acid and the mixture was vacuum filtered. The recovered crystals were washed with ethyl acetate and dissolved in 50ml of refluxing isopropanol. The solution was iced and vacuum filtered and the product was dried to obtain 6.8 g of 2-methyl-5-[N,N-dimethylcarbamoyloxy)- methyl]-thiazole hydrochloride melting at 130° C.

Analysis: $C_8H_{13}N_2O_2SCl$

Calculated: %C, 40.59; H, 5.54; N, 11.83; S, 13.55; Cl, 14.98; Found: %C,40.3; H,5.7; N,11.9; S,13.5; Cl,15.2.

EXAMPLE 3

2-methyl-5-(N-phenylcarbamoyloxymethyl)-thiazole hydrochloride

A mixture of 2.6 g of 2-methyl-5-hydroxymethyl-thiazole, 2.6 g of phenyl isocyanate, 26 ml of anhydrous tetrahydrofuran and 1 ml of triethylamine was refluxed for one hour, cooled to room temperature and then evaporated to dryness under reduced pressure. The residue was dissolved in hot ethyl acetate and the solution was added to ethyl acetate saturated with hydrochloric acid. The mixture was filtered and the crystals were dried to obtain 5 g of crystals which were crystallized from ethanol to obtain 3.2 g of 2-methyl-5-(N-phenylcarbamoyloxy -methyl)-thiazole hydrochloride melting at 160° C.

Analysis: $C_{12}H_{13}N_2O_2$ SCl Calculated: %C, 50.60; H, 4.60; N, 9.83; Cl, 12.44; S, 11.25; Found: %C, 50.5; H, 4.6; N, 9.8; Cl, 12.7; S, 11.2.

EXAMPLE 4

2-methyl-5-(N-methylcarbamoyloxypropyl)-thiazole

STEP A: 3-(2-methyl-5-thiazolyl)-2-propenoic acid

A mixture of 29 g of 2-methyl-5-thiazolecarboxaldehyde, 30 ml of pyridine, 29 g of malonic acid and 30 drops of pyridine was heated at 100°–110° C for 5 hours and after cooling to room temperature, the mixture was poured into 500 ml of water. The pH of the solution was adjusted to 3 by addition of N sulfuric acid and the precipitate formed was recovered by vacuum filtration and was dried to obtain 27.8 g of 3-(2-methyl-5-thiazolyl)-2-propenoic acid which were crystallized from 10% aqueous ethanol to obtain 23.8 g of the said product melting at 204° C.

STEP B: 2-methyl-5-thiazolepropanoic acid

A current of hydrogen was passed through a mixture of 10 g of the product of Step A, 260 ml of ethanol, 15 ml of triethylamine and 5 g of activated carbon containing 10% by weight of palladium for one hour and the mixture was filtered. The filter was washed with ethanol and the filtrate was evaporated to dryness to obtain 13.3 g of a colorless oil which was dissolved in 100 ml of water. Sulfur dioxide was bubbled through the solution until the pH became acid and nitrogen was bubbled therethrough to remove excess sulfur dioxide. The crystals formed were recovered by vacuum filtration and were dried to obtain 7.1 g of product which was crystallized from ethyl acetate to obtain 6.5 g of 2-methyl-5-thiazolepropanoic acid melting at 120° C.

STEP C: methyl 2-methyl-5-thiazolepropanoate

A mixture of 31.7 g of 2-methyl-5-thiazolepropanoic acid, 3.2 ml of concentrated sulfuric acid and 300 ml of methanol was refluxed for 16 hours and was then concentrated to dryness. The residue was taken up in 100 ml of water and the pH was adjusted to 12–13 with addition of concentrated ammonium hydroxide. The mixture was extracted with methylene chloride and the extracts were dried over magnesium sulfate and was evaporated to dryness under reduced pressure to obtain 35 g of raw methyl 2-methyl-5-thiazolepropanoate. Its hydrochloride had a melting point of 115° C.

STEP D: 2-methyl-5-thiazole-propanol

A mixture of 125 ml of tetrahydrofuran and 3.42 g of lithium aluminum hydride was cooled to about 10° C and a mixture of 10.9 g of methyl 2-methyl-5-thiazole-propanoate in 70 ml of tetrahydrofuran was slowly added thereto with stirring while keeping the temperature between 10–15° C. The mixture was then stirred for about 30 minutes and tetrahydrofuran containing 20% of water was slowly added. The mixture was filtered and the filter was washed with ethyl acetate. The filtrate was dried over magnesium sulfate and concentrated to dryness under reduced pressure to obtain 8.4 g of a raw product which was rectified under reduced pressure to obtain 6.4 g of 2-methyl-5-thiazole-propanol with a boiling point of 106° C at 0.05 mm Hg.

Analysis: $C_7H_{11}NOS$ Calculated: %C, 53.47; H, 7.05; N, 8.90; S, 20.39; Found: %C, 53.2; H, 7.2; N, 8.6; S, 20.1.

STEP E: 2-methyl-5-(N-methylcarbamoyloxypropyl)-thiazole

A mixture of 45 g of 2-methyl-5-thiazolepropanol, 20 ml of tetrahydrofuran, 0.7 ml of triethylamine and 5 ml of methyl isocyanate was refluxed for 16 hours and was then concentrated to dryness under reduced pressure. The residue was dissolved in 6 ml of refluxing ethyl acetate and then was cooled and iced. The mixture was vacuum filtered and the recovered crystals were dried to obtain 5.25 g of white crystals which were crystallized from ethyl acetate to obtain 4.2 g of 2-methyl-5-(N-methylcarbamoyloxypropyl)-thiazole melting at 86° C.

Analysis: $C_9H_{14}N_2O_2S$ Calculated: %C, 50.49; H, 6.59; N, 13.07; S, 14.91; Found: %C, 50.5; H, 6.8; N, 13.0; S, 14.8.

EXAMPLE 5

2-propyl-5-(N-methylcarbamoyloxypentyl)-thiazole

STEP A: 2-propyl-5-thiazolecarboxaldehyde

A mixture of 21 g of 2-propyl-5-hydroxymethyl-thiazole, 1000 ml of benzene and 100 g of manganese dioxide was stirred at room temperature for 3 hours and after the addition of another 40 g of manganese dioxide, the mixture was stirred for 2 hours at room temperature. Another 20 g of manganese dioxide were added to the reaction mixture which was then stirred for 16 hours at room temperature and was filtered. The filter was washed with methylene chloride and the filtrate was evaporated to dryness under reduced pressure to obtain 18.5 g of 2-propyl-5-thiazolecarboxaldehyde.

STEP B: ethyl 5-(2-propyl-5-thiazolyl)-2,4-pentadienoate

A mixture of 100 ml of anhydrous tetrahydrofuran and 5.5 g of sodium hydride dispersed in 50% by weight of an oil was stirred at 0° C and then 28.5 g of triethyl phosphonocrotonate in 40 ml of tetrahydrofuran were added thereto. Then a mixture of 17.5 of 2-propyl-5-5hiazolecarboxaldehyde in 40 ml of tetrahydrofuran was slowly added to the mixture which was then stirred for 15 minutes at 0° C and then was poured into 300ml of a ice-water mixture. The mixture was extracted with methylene chloride and the organic extracts were washed with water, dried over magnesium sulfate and concentrated to dryness under reduced pressure to obtain 35 g of raw product. The latter was chromatographed over silica gel and was eluted with ethyl acetate to obtain 16 g of ethyl 5-(2-propyl-5-thiazolyl) -2,4-pentadienoate melting at 52° C.

STEP C: ethyl 2-propyl-5-thiazolepentanoate

Hydrogen was added with stirring for 2 hours to a mixture of 25 g of ethyl 5-(2-propyl-5-thiazolyl)-2,4-pentadienoate, 250 ml of ethanol and 12.5 g of activated carbon containing 10% palladium and the mixture was filtered. The fiter was washed with ethanol and the filtrate was evaporated to dryness under reduced pressure to obtain 23 g of raw ethyl 2-propyl -5-thiazolepentanoate.

STEP D: 2-propyl-5-thiazolepentanol

A mixture of 23 g of ethyl 2-propyl-5-thiazolepentanoate in 150 ml of anhydrous tetrahydrofuran was added at 10° C with stirring to a mixture of 250 ml of tetrahydrofuran and 5 g of lithium aluminum hydride and the mixture was stirred for 30 minutes. Excess hydride was destroyed by the slow addition of tetrahydrofuran containing 10% water while holding the temperature at 15°–20° C and then an aqueous solution saturated with sodium potassium tartrate was slowly added. The mixture was filtered and the filter was washed with ethyl acetate. The filtrate was dried over magnesium sulfate and evaporated to dryness under reduced pressure to obtain 20 g of a pale yellow oil which was rectified to obtain 15 g of 2- propyl-5-thiazolepentanol in the form of a colorless oil with a boiling point of 122° C at 0.1 mm Hg.

Analysis: $C_{11}H_{19}NOS$ Calculated: %C, 61.93; H, 8.98; N, 6.56; S, 15.03; Found %C, 61.7; H, 9.2; N, 6.3; S, 14.9.

STEP E: 2-propyl-5-(N-methylcarbamoyloxypentyl)-thiazole

A mixture of 5 g of 2-propyl-5-thiazolepentanol, 35 ml of tetrahydrofuran, 0.7 ml of triethylamine and 3.5 ml of methyl isocyanate was refluxed for 16 hours and was cooled to room temperature and evaporated to dryness under reduced pressure. The 6.5 g of raw product were dissolved in 20 ml of refluxing cyclohexane and the solution was treated with activated carbon. The residue was redissolved in refluxing cyclohexane and the solution was allowed to cool and then was iced. The mixture was vacuum filtered and the crystals recovered were dried to obtain 5.9 g of 2-propyl-5-(N-methylcarbamoyloxypentyl)-thiazole melting at 45° C.

Aanlysis: $C_{13}H_{22}N_2O_2S$ Calculated: %C, 57.75; H, 8.2; N, 10.36; S, 11.86; Found %C, 57.4; H, 8.1; N, 10.5; S, 12.

EXAMPLE 6

Tablets were prepared containing 500 mg of 2-methyl-5-(N-methylcarbamoyloxymethyl)-thiazole or 2-methyl-5-(N-methylcarbamoyloxypropyl) -thiazole and sufficient amount of an excipient consisting of talc, lactose, rice starch, wheat starch, modified starch and magnesium stearate.

Gelules were prepared containing 500 mg of 2-propyl-5-(N-methylcarbamoyloxypentyl)-thiazole or 2-methyl-5-(N-methylcarbamoyloxymethyl)-thiazole and sufficient excipient of talc, magnesium stearate and aerosil to obtain a final weight of 525 mg.

PHARMACOLOGICAL STUDY

A. Acute toxicity

The acute toxicity was determined on groups of 10 mice weighing between 18 to 22 g and the product was administered intraperitoneally as a suspension in carboxymethylcellulose. The animals were observed for one week and the average lethal doses ($DL_{50}$) were found and are reported in Table I.

TABLE I

| Compound of Example | $DL_{50}$ in mg/kg |
|---|---|
| 1 | ≃ 1,500 |
| 2 | ≃ 350 |
| 3 | ≃ 250 |
| 4 | > 1,000 |

B. Antilipolytic activity

Male rats of the Sprague Dawley SPF strain weighing about 180 to 200 g were starved for 24 hours and then were given the product of Example 1 orally. One hour after the oral administration, the animals were killed by carotidienne section and samples of the blood were obtained to determine the dosage of free fatty acids. The extraction of the free fatty acids were made by the technique of Dole [J. Clin. Invest., Vol. 38 (1959), p. 1544–1554] as modified by Trout et al [J. Lipid. Res., Vol. 1 (1960) p. 199–202]. The plasmatic extract free of phospholipids was colorimetrically determined by the method of Anthonis [J. Lipid. Res., Vol. 6 (1965), p. 307–312]. Under these test conditions, the doses which reduced by 50% the level of free fatty acids in the treated animals as compared to the controls ($DA_{50}$) were found and are reported in Table II.

TABLE II

| Compound of Example | $DA_{50}$ in mg/kg |
|---|---|
| 1 | ≃ 5 |
| 2 | ≃ 5 |
| 3 | ≃ 7 |
| 4 | > 50 |

C. Cutaneous vasodilatatory effect

The cutaneous vasodilatatory effect was determined on albino guinea pig and was manifested by the appearance of a reddening of the ears after a certain latency time. The animals were not fed and the product of Example 1 was orally administered. The time for the reddening appearance of the ears and the duration and intensity was noted on a subjective sale of 1 to 3. At a dose of 20 mg/kg, the latency period was 21 minutes for a duration of 40 minutes and an intensity of 2.8. The cutaneous vasodilatatory activity is manifested at doses clearly superior to antilipolytic doses.

D. Antibradykinetic activity in vitro

The antibradykinetic activity in vitro was determined by the effect on the guinea pig ileon placed in a tank containing Tyrode solution of a bradykinin solution. From the first, the sensibility of the guinea pig ileon to bradykinin is determined by adding to the tank 5 or 10 ng of bradykinin per ml of Tyrode solution and then, the ileon having reacted to bradykinin, the dose of the test product, added in increasing quantities which will reduce by 50% the contraction of the ileon due to bradykinin is determined. The value found were $1.0 \times 10^{-3}$ M/l and $1.7 \times 10^{-4}$ M/l for the products of Examples 1 and 3, respectively which means the products have a clear antibradykinetic activity.

Various modifications of the products and methods of the invention may be made without departing from the spirit or scope thereof and it is to be understood that the invention is intended to be limited only as defined in the appended claims.

We claim:

1. A compound selected from the group consisting of a thiazole of the formula

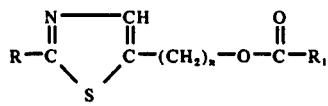

wherein R is alkyl of 1 to 5 carbon atoms and $R_1$ is selected from the group consisting of $-NH_2$, $-NH-Alk$,

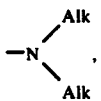

phenylamino and diphenylamino, Alk is alkyl of 1 to 4 carbon atoms and $n$ is an integer from 1 to 6 and their non-toxic, pharmaceutically acceptable acid addition salts.

2. A compound of claim 1 wherein $R_1$ is selected from the group consisting of methylamino, dimethylamino, phenylamino and diphenylamino and $n$ is 1.

3. A compound of claim 1 selected from the group consisting of 2-methyl-5-(N-methylcarbamoyloxymethyl)-thiazole and its non-toxic, pharmaceutically acceptable acid addition salts.

4. A compound of claim 1 selected from the group consisting of 2-methyl-5-(N,N-dimethylcarbamoyloxymethyl)-thiazole and its non-toxic, pharmaceutically acceptable acid addition salts.

5. A compound of claim 1 selected from the group consisting of 2-methyl-5-(N-phenylcarbamoyloxymethyl)-thiazole and its non-toxic, pharmaceutically acceptable acid addition salts.

6. A compound of claim 1 selected from the group consisting of 2-methyl-5-(N-methylcarbamoyloxypropyl)-thiazole and its non-toxic, pharmaceutically acceptable acid addition salts.

7. A compound of claim 1 selected from the group consisting of 2-propyl-5-(N-methylcarbamoyloxypentyl)-thiazole and its non-toxic, pharmaceutically acceptable acid addition salts.

8. A hypolipemiant composition comprising a hypolipemically effective amount of at least one compound of claim 1 and a pharmaceutical carrier.

9. A method of inducing hypolipemic acitivity in warm-blooded animals comprising administering to warm-blooded animals a hypolipemically effective amount of at least one compound of claim 1.

10. The method of claim 9 wherein $n$ is 1 and $R_1$ is selected from the group consisting of methylamino, dimethylamino, phenylamino and diphenylamino.

11. The method of claim 9 wherein the compound is selected from the group consisting of 2-methyl-5-(N-methylcarbamoyloxymethyl) -thiazole and its non-toxic, pharmaceutically acceptable acid addition salts.

12. The method of claim 9 wherein the compound is selected from the group consisting of 2-methyl-5-(N,N-dimethylcarbamoyloxymethyl) -thiazole and its non-toxic, pharmaceutically acceptable acid addition salts.

13. The method of claim 9 wherein the compound is selected from the group consisting of 2-methyl-5-(N-phenylcarbamoyloxymethyl) -thiazole and its non-toxic, pharmaceutically acceptable acid addition salts.

14. The method of claim 9 wherein the compound is selected from the group consisting of 2-methyl-5-(N-methylcarbamoyloxypropyl) -thiazole and its non-toxic, pharmaceutically acceptable acid addition salts.

15. The method of claim 9 wherein the compound is selected from the group consisting of 2-propyl-5-(N-methylcarbamoyloxypentyl) -thiazole and its non-toxic, pharmaceutically acceptable acid addition salts.

* * * * *